United States Patent
Li et al.

(10) Patent No.: US 9,335,313 B2
(45) Date of Patent: May 10, 2016

(54) IMMATURE EAR PHOTOMETRY IN MAIZE

(71) Applicant: PIONEER HI BRED INTERNATIONAL INC, Johnston, IA (US)

(72) Inventors: Guofu Li, Johnston, IA (US); Travis A. Hanselman, Johnston, IA (US); Jacque Hockenson, Johnston, IA (US); Dale F. Loussaert, Clive, IA (US); Timothy Michael Moriarty, Urbandale, IA (US); Rachael Woods, Johnston, IA (US)

(73) Assignee: PIONEER HI BRED INTERNATIONAL INC., Johnston, IA (US)

( * ) Notice: Subject to any disclaimer, the term of this patent is extended or adjusted under 35 U.S.C. 154(b) by 24 days.

(21) Appl. No.: 14/368,966

(22) PCT Filed: Dec. 26, 2012

(86) PCT No.: PCT/US2012/071617
§ 371 (c)(1),
(2) Date: Jun. 26, 2014

(87) PCT Pub. No.: WO2013/101806
PCT Pub. Date: Jul. 4, 2013

(65) Prior Publication Data
US 2014/0376782 A1    Dec. 25, 2014

Related U.S. Application Data

(60) Provisional application No. 61/581,949, filed on Dec. 30, 2011.

(51) Int. Cl.
*G01N 33/00* (2006.01)
*C12N 15/82* (2006.01)
*G06T 7/00* (2006.01)

(52) U.S. Cl.
CPC ........ *G01N 33/0098* (2013.01); *C12N 15/8209* (2013.01); *G06T 7/0012* (2013.01); *G06T 7/0079* (2013.01); *G06T 2207/30004* (2013.01)

(58) Field of Classification Search
None
See application file for complete search history.

(56) References Cited

U.S. PATENT DOCUMENTS

2007/0186313 A1* 8/2007 Lightner ............ A01H 1/04
                                                        800/320.1
2009/0046890 A1* 2/2009 Hausmann ........... G06T 7/0012
                                                        382/100

FOREIGN PATENT DOCUMENTS

| JP | 04145309 | 5/1992 |
|---|---|---|
| WO | 2009/023110 A1 | 2/2009 |
| WO | 2010/132731 A1 | 11/2010 |

OTHER PUBLICATIONS

Jia. "Seed Maize Quality Inspection with Machine Vision." Proc. SPIE 1989, Computer Vision for Industry, Dec. 17, 1993, pp. 288-295.*

(Continued)

*Primary Examiner* — Jon Chang

(57) ABSTRACT

Methods for evaluating one or more immature ears of maize are presented in which digital imagery and image processing are used to assess physical properties of immature maize ears that are correlated with yield and other yield-related traits. Also provided are methods for identifying leads using immature ear photometry.

19 Claims, 10 Drawing Sheets

Images of immature ear(s) for analysis A) single B) multiple

(56) References Cited

OTHER PUBLICATIONS

Shyu et al. "Image Analysis for Mapping Immeasurable Phenotypes in Maize." IEEE Signal Processing Magazine, vol. 24, issue 3, May 2007, pp. 115-118.*

Kiratiratanapruk et al. "Color and Texture for Corn Seed Classification by Machine Vision." International Symposium on Intelligent Signal Processing and Communications Systems, Dec. 7, 2011, pp. 1-5.*

English Abstract of JP04145309.

Chi-Ren Shyu et al. "Image Analysis for Mapping Immeasurable Phenotypes in Maize [Life Sciences]", IEEE Signal Processing Magazine, IEEE Service Center, Piscataway, NJ, US, vol. 24, No. 3, May 1, 2007. pp. 115-118, XP011201392. ISSN: 1053-5888 section "A Phenotype Mapping System" figure 1.

Jia J. "Seed maize quality inspection with machine vision", SPIE—Computer Vision for Industry., vol. 1989, Jun. 24, 1993, pp. 288-295, XP002507235, ISBN: 978-0-8194-1238-6 abstract section 3.2 figures 5, 8, 10.

International Search Report—PCT/US2012/071617—Issue Mar. 19, 2013.

* cited by examiner

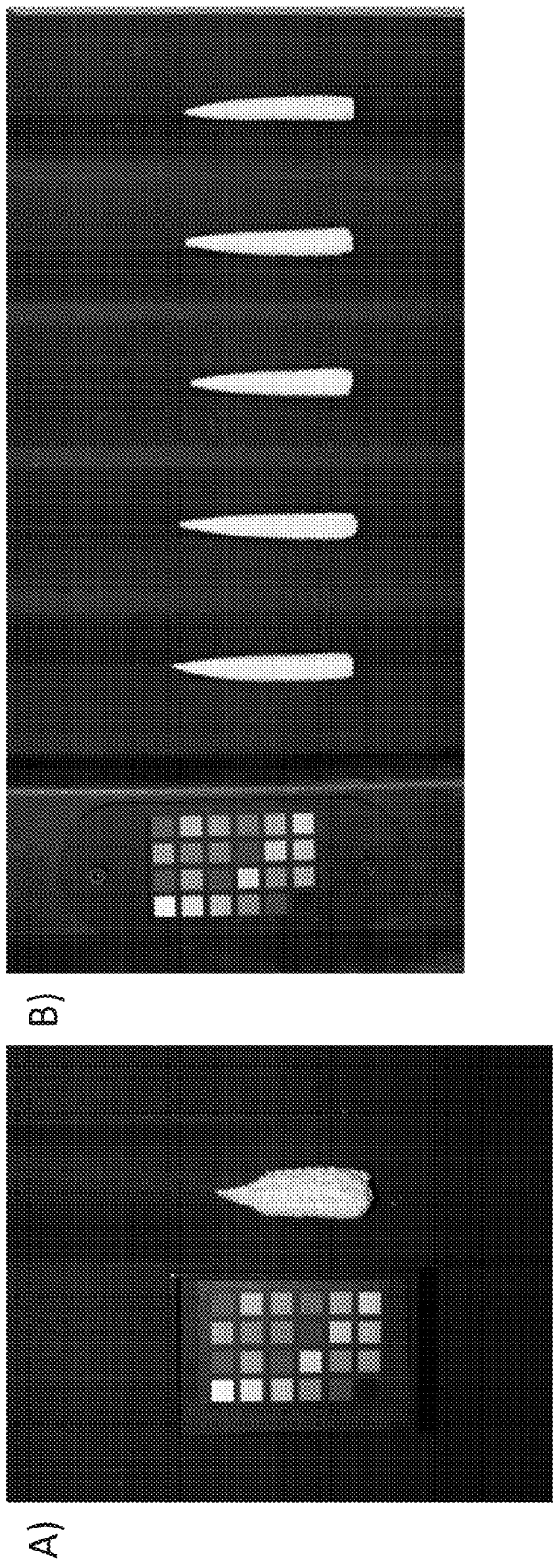
FIG. 1: Images of immature ear(s) for analysis A) single B) multiple

FIG. 2: A) Single ear image  B) Multi-ear image
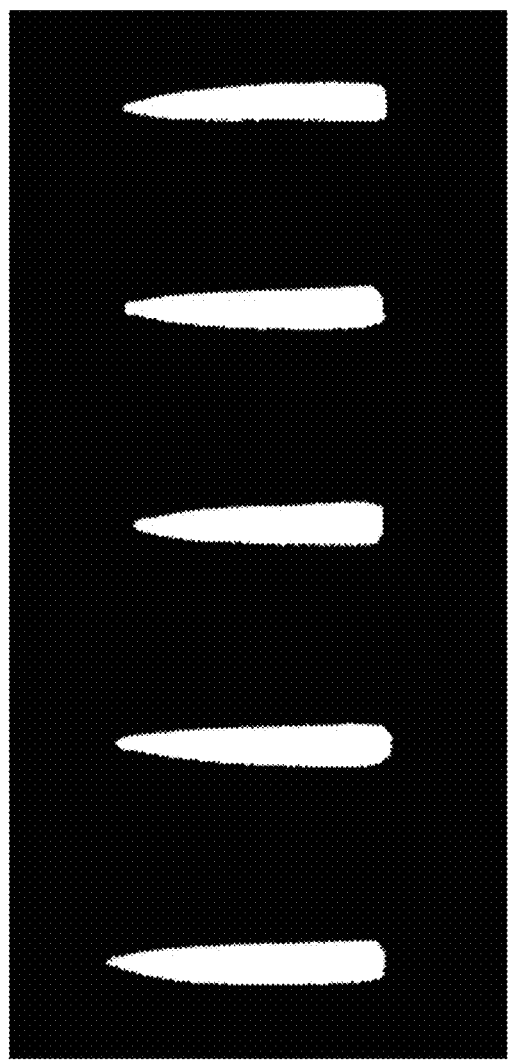
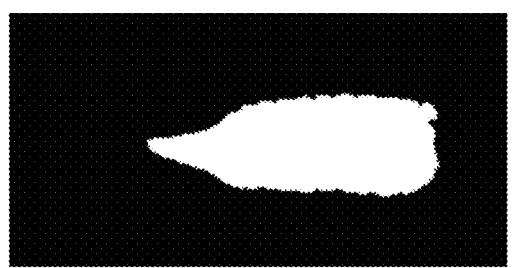

FIG. 10
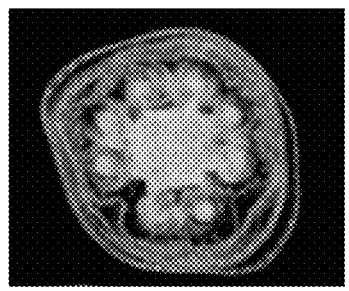
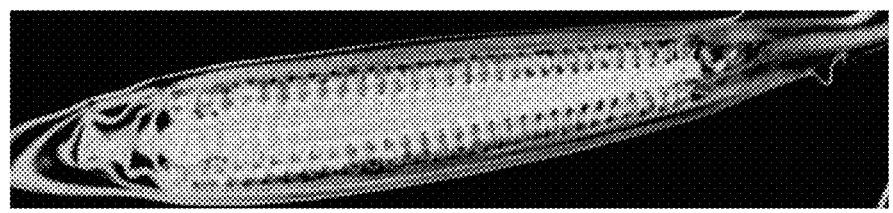
B
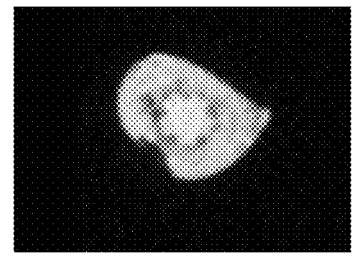
A

IMMATURE EAR PHOTOMETRY IN MAIZE

CROSS REFERENCE TO RELATED APPLICATIONS

This application claims the benefit of U.S. Provisional Application No. 61/581,949, filed Dec. 30, 2011, which is incorporated by reference in its entirety.

FIELD OF THE DISCLOSURE

The present disclosure relates to a method for assessing maize plants for yield or yield related traits by evaluating immature ears of maize plants using digital imagery and photometric analysis.

BACKGROUND OF THE DISCLOSURE

There are well described approaches for evaluating yield or yield-related traits in maize by maize plant performance in the field (e.g. in yield trials), whether the maize plants are produced conventionally through breeding practices or via genetic engineering. However, field testing requires significant time, manpower, acreage, and monetary resources, which hinders the number of maize plants that can be evaluated in any given period of time. The problem remains as to how to rapidly evaluate maize plants for yield or yield related traits using fewer resources.

SUMMARY OF THE DISCLOSURE

In one embodiment, methods for evaluating maize plants by assessing physical properties of immature ears are provided herein. In these methods, a digital image is acquired of one or more immature ears of a maize plant; the digital image is processed; physical properties of the immature ear(s) are measured from the processed digital image; and the maize plant is evaluated based on the physical property(s) of the immature ear(s).

The measured physical property of the immature ear(s) may include without limitation: area, length, width, perimeter, color, silk count, spikelet number, size distribution, and tapering of the ear; and the digital image may be processed using binary segmentation.

The digital image may be acquired using an image sensor or by scanning an analog image. If acquired by an image sensor, the image sensor may be a charge coupled device (CCD) image sensor, a digital camera, a video camera, a color sensor, a laser/light beam sensor, an X-ray scanner/sensor, or an ultrasonic sensor, and the digital image may be acquired under controlled lighting conditions or may be acquired using algorithmically or manually determined lighting conditions. The image sensor may be configured to image one or more immature ears in their entirety or smaller subsections of one or more immature ears.

The digital image maybe acquired non-destructively.

The methods may further comprise predicting mature ear yield for a maize plant based on a physical property of an immature ear.

In another embodiment, methods for evaluating maize plants, which may or may not contain one or more transgenes of interest, for yield and/or a yield related trait are presented in which one or more maize plants are grown, either in a field or in a controlled environment setting; digital images are acquired of one or more immature ears of the one or more maize plants; the digital images are processed using binary segmentation; physical properties of the one or more immature ears are measured from the processed digital images; and the one or more maize plants are evaluated for yield and/or a yield related trait based on the physical property(s) of the one or more immature ears.

The measured physical property of the immature ear(s) may include without limitation: area, length, width, perimeter, color, silk count, spikelet number, size distribution, and tapering of the ear.

The digital image may be acquired using an image sensor or by scanning an analog image. If acquired by an image sensor, the image sensor may be a charge coupled device (CCD) image sensor, a digital camera, a video camera, a color sensor, a laser/light beam sensor, an X-ray scanner/sensor, or an ultrasonic sensor, and the digital image may be acquired under controlled lighting conditions or may be acquired using algorithmically or manually determined lighting conditions. The image sensor may be configured to image one or more immature ears in their entirety or smaller subsections of one or more immature ears.

The one or more immature ears may be harvested, either manually or with a machine, or may remain on the plant.

The yield related trait may include, without limitation, biomass, nitrogen stress tolerance, or drought tolerance.

The maize plants may be exposed to nitrogen and/or water limiting conditions.

In another embodiment, methods for high-throughput analysis of the effect of a transgene of interest (or a construct containing a transgene of interest) on yield or a yield related trait in maize are provided in which a population of transgenic maize plants is grown in a controlled environment setting; a digital image is acquired of an immature maize ear from two or more maize plants in the population; the digital images are processed using binary segmentation; a mean or median value of at least one measured physical property and the coefficient of variation are calculated for the population of transgenic plants; and a statistical test is performed to determine if there is a significant difference between a single member of the population of transgenic plants and the mean or median value for the population of transgenic plants with respect to the at least one physical property.

The measured physical property of the immature ear(s) may include without limitation: area, length, width, perimeter, color, silk count, spikelet number, size distribution, or tapering of the ear.

The digital image may be acquired using an image sensor or by scanning an analog image. If acquired by an image sensor, the image sensor may be a charge coupled device (CCD) image sensor, a digital camera, a video camera, a color sensor, a laser/light beam sensor, an X-ray scanner/sensor, or an ultrasonic sensor, and the digital image may be acquired under controlled lighting conditions or may be acquired using algorithmically or manually determined lighting conditions. The image sensor may be configured to image one or more immature ears in their entirety or smaller subsections of one or more immature ears.

The one or more immature ears may be harvested, either manually or with a machine, or may remain on the plant.

The yield related trait may include, without limitation, biomass, nitrogen stress tolerance, or drought tolerance.

The maize plants may be exposed to nitrogen and/or water limiting conditions.

In another embodiment, methods of evaluating an immature reproductive part of a crop plant to assess the effect of a transgene or a recombinant nucleic acid construct on seed yield in the crop plant are provided. In these methods, digital images of the immature reproductive part of the crop plant are obtained without physically removing the part from the crop plant, and the digital images are analyzed to assess the effect of the transgene or the recombinant nucleic acid construct on seed yield. The reproductive part may be an immature ear of a maize plant.

The transgene may be overexpressed.

The recombinant nucleic acid construct may be an RNAi construct.

BRIEF DESCRIPTION OF THE DRAWINGS

The disclosure can be more fully understood from the following detailed description and the accompanying drawings FIG. 1 shows images of immature ear(s) for analysis. A) represents a single ear image, and B) shows a multi-ear image.

FIG. 2 shows images following binary segmentation processing in preparation for measurement analysis. A) represents a single ear image, and B) shows a multi-ear image.

FIG. 10 shows images of immature ears obtained from X-ray imaging. (A) shows a longitudinal and a cross-sectional view of a "younger" immature ear, while (B) shows a longitudinal and a cross-sectional view of an "older" yet still immature ear.

DETAILED DESCRIPTION

Figure 3:
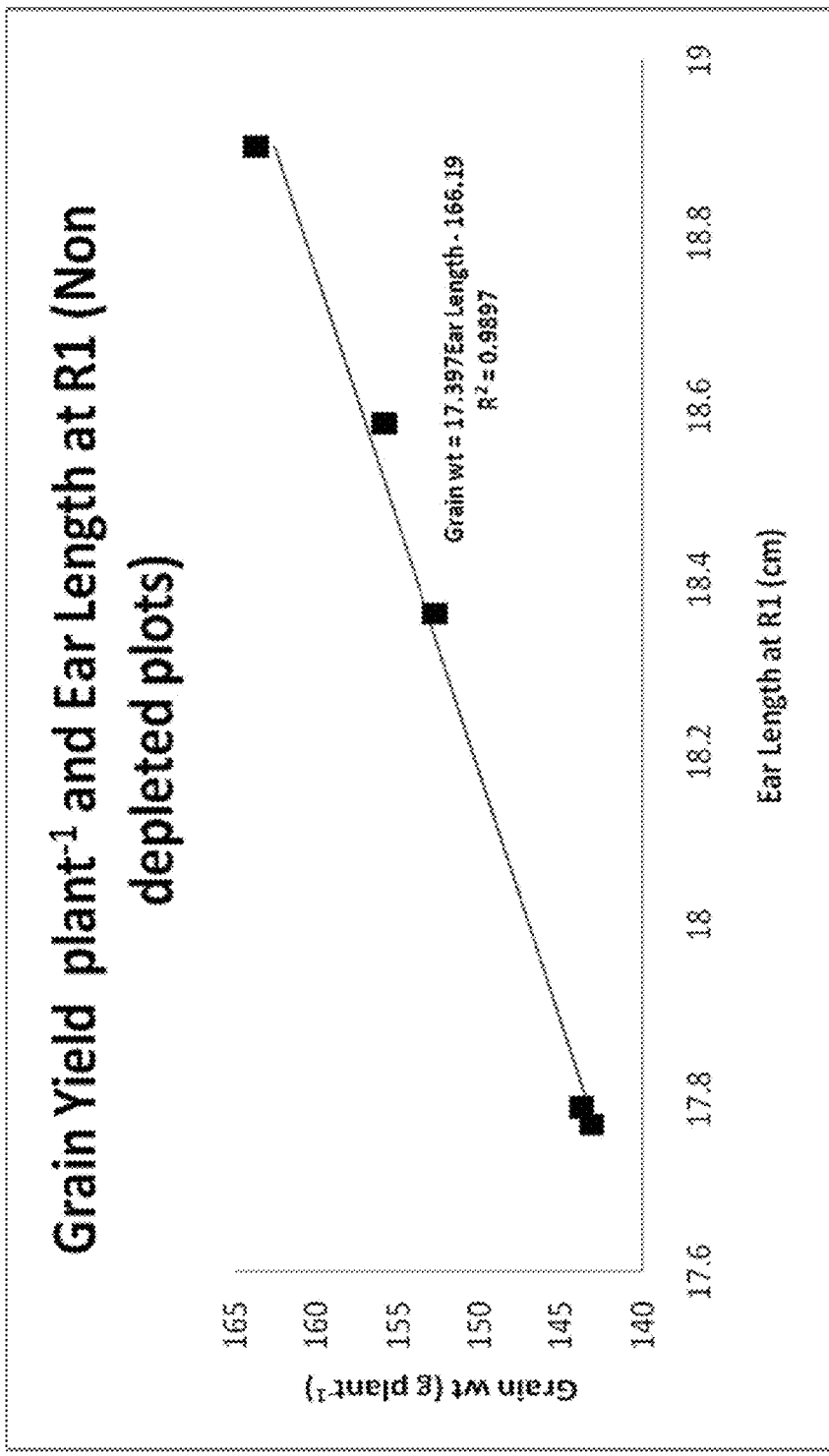
FIG. 3 shows the relationship between grain yield per plant and ear length at the R1 stage in nitrogen non-depleted plots (normal nitrogen conditions).
Figure 4:
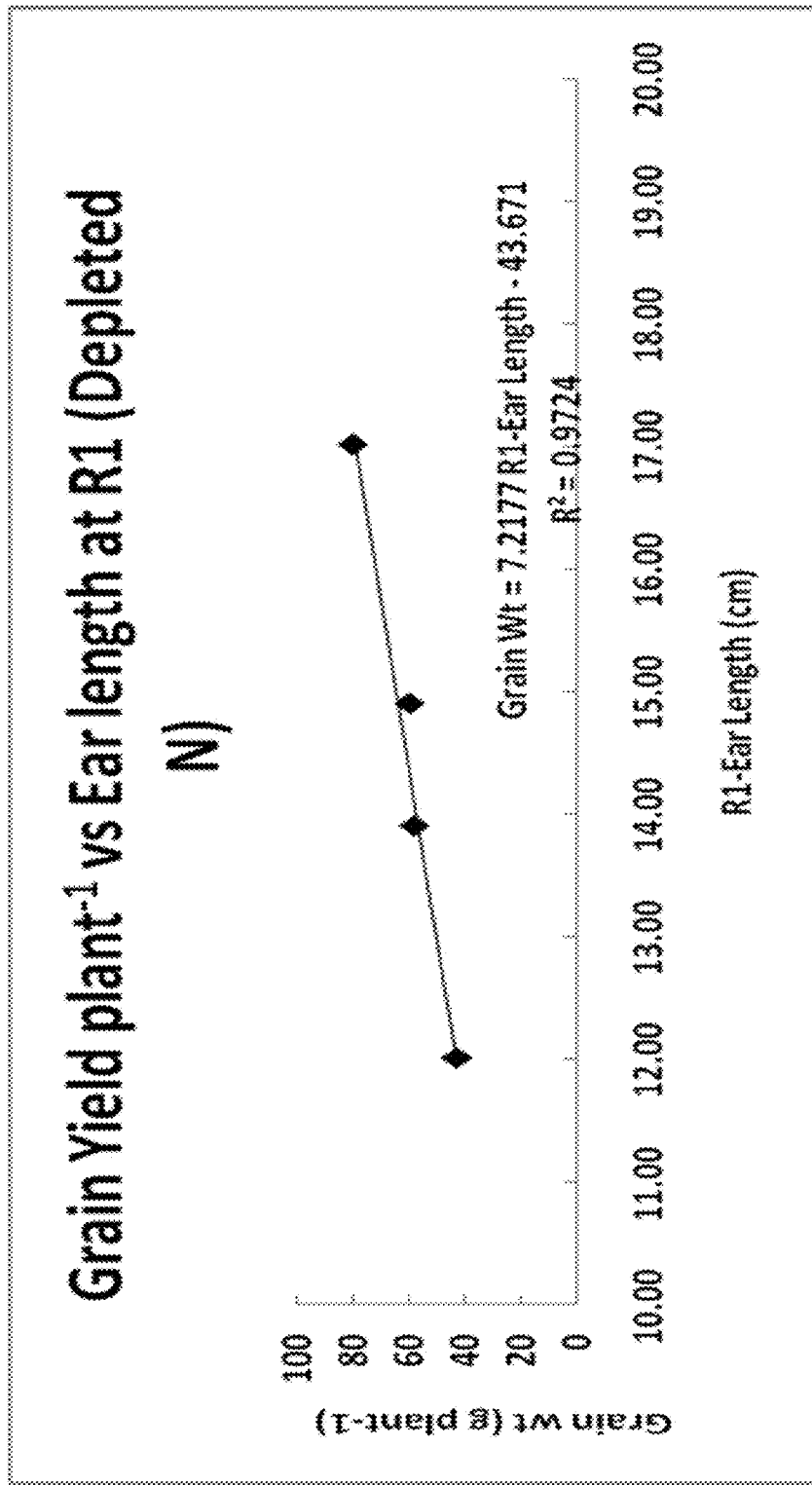
FIG. 4 shows the relationship between grain yield per plant and ear length at the R1 stage for nitrogen-depleted plots.
Figure 5:
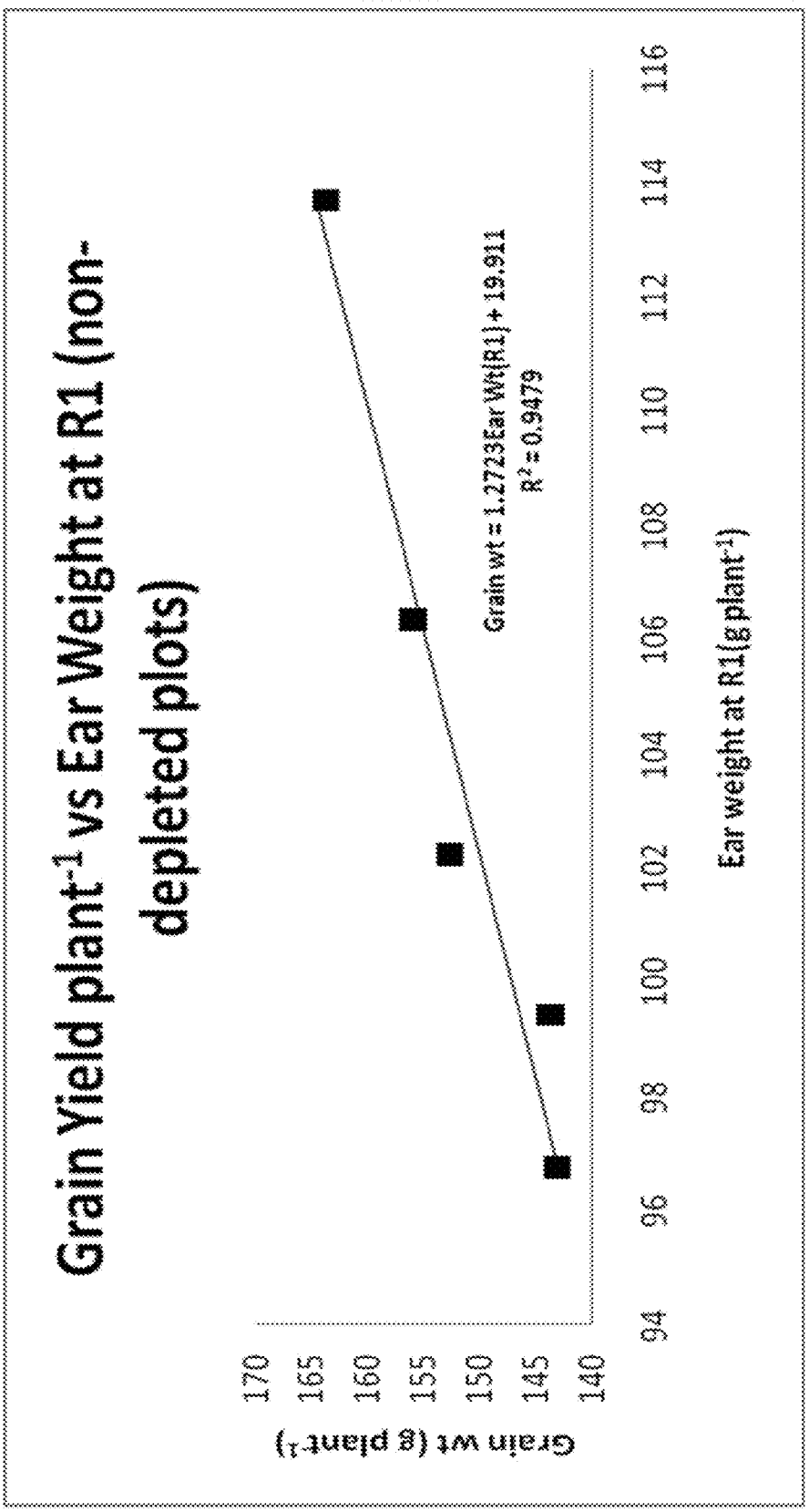
FIG. 5 shows the relationship between grain yield per plant and ear weight at the R1 stage in nitrogen non-depleted plots (normal nitrogen conditions).
Figure 6:
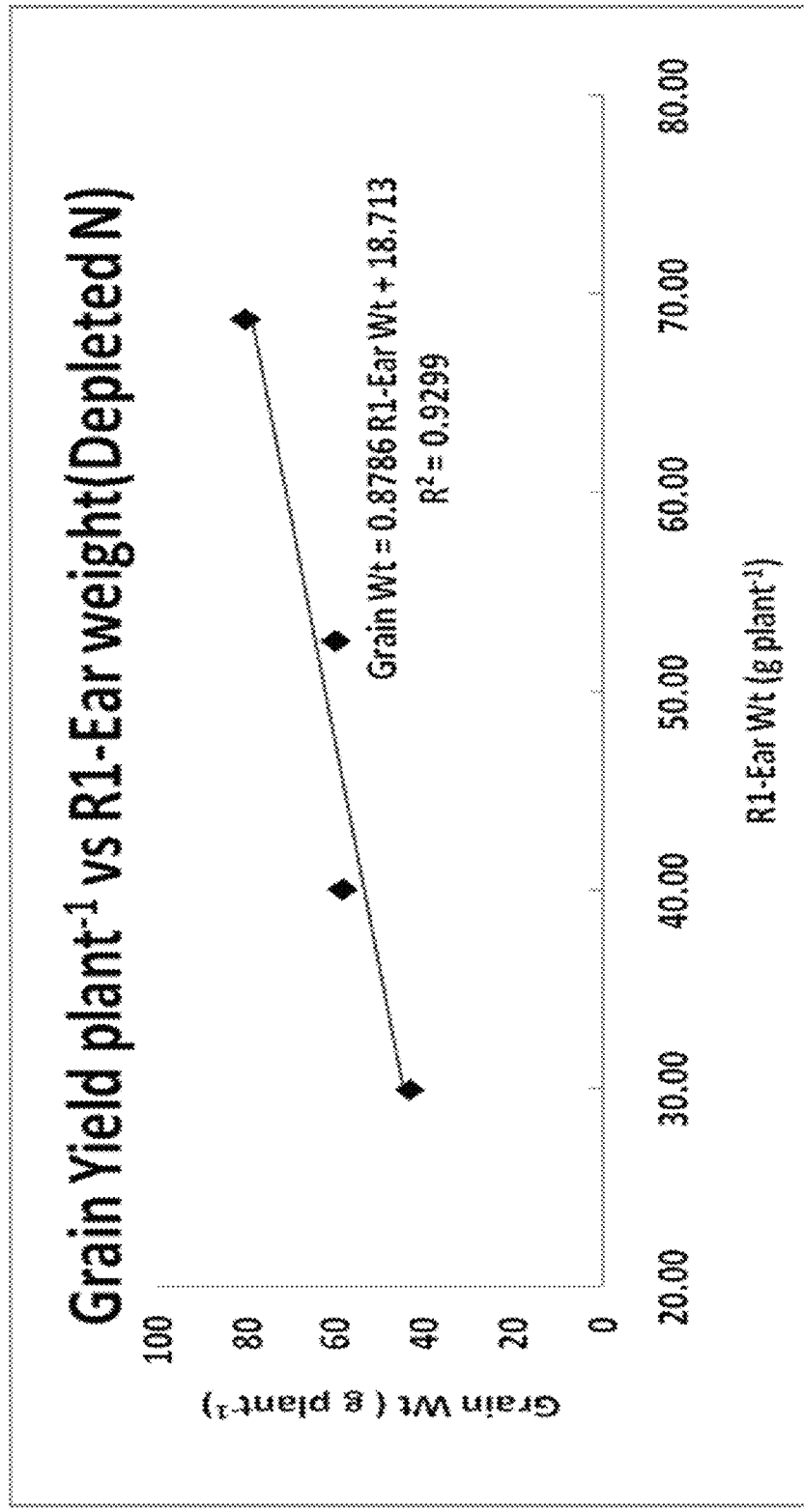
FIG. 6 shows the relationship between grain yield per plant and ear weight in nitrogen-depleted plots.

The disclosure of each reference set forth herein is hereby incorporated by reference in its entirety to the extent they relate to the methods practiced herein.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

Overview

Because immature ear traits correlate with seed yield and other mature ear traits, image analysis of immature ears provides a reasonable means for predicting field performance such as but not limited to seed yield and ear weight as well as other reproductive parameters such as but not limited to anthesis-silking interval.

Digital imaging and appropriate image processing (e.g. binary segmentation) allow for high throughput quantitative measurement of immature ear phenotypes of individual maize plants. Immature ear phenotypes have shown to be correlated with yield and yield-related traits. Applications of immature ear photometry and binary image segmentation may include but are not limited to: studying genetic variation on a plant-to-plant basis; screening plants for yield, yield related traits, or stress tolerance (e.g. as part of a breeding program); quantifying plant-to-plant variability for stress tolerance; characterizing ear type for direct breeding; measuring genotypic response to micro-environmental variation in the field, rapidly evaluating the effects of introduced transgenes and/or genetic regions (QTL) on yield and/or yield related traits; determining the degree to which progeny of a cross are phenotypically similar to each parent; etc.

Plant Growth

"Environmental conditions" refer to conditions under which the plant is grown, such as the availability of water, availability of nutrients (for example nitrogen), or the presence of insects or disease.

Plants may be grown in a "controlled environment setting", such as a greenhouse or growth chamber, where water and nutrient availability is controlled as are other factors including but not limited to: temperature, exposure to extreme weather elements, and pests. Alternatively, plants may be grown in a screenhouse or field environment in which there is little to no control over environmental effects.

Plants and plant parts (e.g. immature ears) that are evaluated using the methods of the disclosure may or may not contain one or more transgenes of interest.

With respect to transgene-containing plants, an event population of transgenic (T0) plants resulting from transformed maize embryos may be grown in a environmentally-controlled greenhouse using any of a number of experimental designs to reduce or eliminate environmental error. T0 sister plants may be obtained from the same callus, and the methods of the disclosure may be applied to one or more of the sister plants. A T0 sister plant that is not subject to the methods of the disclosure at the T0 stage may be selected for advanced testing based on sister plant performance and then crossed to a fast growing inbred to obtain seeds (T1) for analysis in the next generation.

Each plant may be identified and tracked through the entire process, and the data gathered from each plant may be automatically associated with that plant. For example, each plant may have a machine-readable label (such as a Universal Product Code (UPC) bar code) which may include information about the plant identity and location in the field or greenhouse.

Image Acquisition

The term "immature ear" generally refers to an ear from the stage at which the first silk has emerged to about 20 days after silking (DAS). The immature ear may be assessed, for example, at 8 DAS when testing is performed in the greenhouse, while assessment in the field may occur at the R1 (first reproductive) stage, or when approximately 1 to about 50 silks are visible, Images may be taken of immature ears that have been removed from the plant through hand or machine harvesting or of immature ears that remain attached to the plant.

The images may be of one ear or multiple ears, or even of smaller subsections of one or more immature ears.

The use of controlled lighting conditions (i.e. lighting conditions that are reproducible) allows for simplification of the use of spectral filter and data standardization; however, without controlled lighting conditions, determinations of lighting conditions, either algorithmic or manual, can be made and additional calibrations can be performed to assist in image processing. The quality of the image (lighting, contrast, color balance, color fidelity etc.) can also be manipulated to improve the image for analysis purposes.

To acquire images, various types of image sensors may be used including but not limited to: a charge coupled device (CCD) image sensor, a camera, a video camera, a color sensor, a laser/light beam sensor, an ultrasonic sensor, an X-ray scanner/sensor, or other type of image sensor. The image sensor may provide for color imaging as color imaging may be desirable where spectral filters are used. The image sensor may provide for imaging across a spectrum wider than or different from the visible spectrum. The image sensor may be configured to image an entire single ear, multiple ears, or smaller subsections of one or more immature ears. If analog images are directly acquired instead of digital images, then the analog images may be converted to digital images through scanning or other means. Alternatively, the amount of light intercepted as the ear moves through a light field could provide an alternate means of either two or three dimensional data collection.

A digital image may be acquired non-destructively, i.e. that an image is acquired of an intact immature ear(s) still on the plant and/or inside husk leaves.

Image Processing

Data may be automatically extracted for each immature ear from digital images using image processing software such as Image Pro Plus (Media Cybernetics, Silver Spring, Md.). Various image processing operations may be performed, such as e.g. techniques or algorithms to delineate image pixels associated with the immature ear objects form the background and/or extraneous debris.

"Binary images" have a limited pixel intensity range consisting of only two possible values: on or off (or one and zero, respectively). "Binary segmentation" involves setting a pixel on or off depending on how it compares to a pre-selected threshold level. The choice of a threshold level can have an impact on the appearance of the resulting binary image. When choosing a threshold level, it is desirable to distinguish the features of interest (i.e. pixels that are "on" or white), e.g. those associated with the immature ear, from background pixels (i.e. pixels that are "off" or black) that lack specimen information. Selection of an appropriate threshold level can be done manually or in an automated fashion, the latter of which is particularly useful for processing large quantities of digital images.

Binary segmentation may be accomplished by comparing acquired images to a previously characterized reference correcting deviations from image quality, isolating and identifying immature ear objects and applying a spatial calibration process to convert pixel unit measurements to metric units of measure. Predefined color and sizing information may be used to isolate the immature ears from foreign material and/or background resulting from the sample holder. A digital filtering process may also be used in the isolation and identification step.

Various methods and algorithms may be used to assist in selection of the threshold level.

Data may be recorded for each whole or subsection of immature ear objects including, without limitation, object area, minor axis length, major axis length, width, perimeter, ear color (such as red, blue, green density), silk count, and/or other information regarding ear size, shape, morphology, location, or color (e.g. spikelet number, size distribution, and tapering of the ear). It is to be appreciated that these items of data may relate to various traits of interest in breeding. For example, ear length and ear width of immature maize ears (i.e. at the R1 stage) has shown to be significantly correlated with grain yield per plant in the field (see EXAMPLE 7; FIGS. 3-6).

FIGS. 1 and 2 show images before and after processing (i.e. binary image segmentation), respectively.

In addition, data may be automatically extracted from images in batch mode enabling labor free processing of many images each day, thereby reducing time and monetary resources required to manually process such numbers of images.

When using an X-ray scanner/sensor, multiple X-ray imaging and analysis techniques may be used, including without limitation: X-ray computed tomography, helical scanning, 3-dimensional reconstruction, and surface planarization.

Data Evaluation

Use of Immature Ear Photometry

The data may be paired with other data so that relationships between the pairs of data may be determined by regression or other statistical techniques used to relate sets of variables. It is to be understood that the type of relationship present between pairs of data may vary and as such different mathematical or statistical tools may be applied. It is to be understood also, that instead of relating two sets of data (pairing), multiple sets of data may be related.

The data extracted from the images may be used to quantify within-plot variability. A "plot" is simply an area where multiple plants of similar genetic background are grown. Within-plot variability describes variations between plants within the plot. Examples of types of within-plot variability measurements include, without limitation, standard error, standard deviation, relative standard deviation, skew, kurtosis, variance, coefficient of variation, and interquartile range.

Immature ear photometry may be used to evaluate maize plants for yield and/or yield related traits. The methods involve growing one or more maize plants, acquiring digital images of immature ear(s), processing the digital images using binary segmentation, determining physical properties of the immature ear(s) using the processed images, and evaluating maize plants for physical properties of immature ears in order to obtain an assessment of yield and/or one or more yield related traits of one or more maize plants relative to other maize plants.

Immature ear photometry may also be used in high-throughput analysis of the effect of a transgene of interest, and/or of a construct containing a transgene of interest, on yield or a yield related trait. These methods combine high throughput transgene function analysis (US Publication Number 2007/0186313 A1) and high throughput T1 phenotyping, as described herein. In these methods, a population of transgenic maize plants is grown in a controlled environment setting; digital images of one or more immature ears are acquired; the digital images are processed using binary segmentation; and the physical properties of the immature ears are evaluated. In one aspect, mean or median values of a physical property (or physical properties) are calculated, as well as a coefficient of variation, for the population of transgenic plants, and a statistical test is performed to determine if there is a significant difference between the mean or median of a single member of the population of transgenic plants as compared to the mean or median value for the population of transgenic plants with respect to the physical property (or properties). The difference may be considered attributable to the transgene of interest. Transgene effect can be measured early in the transgenic variety development process, e.g. as early as the T0 and T1 generations, thereby eliminating the need to generate seed necessary for multi-location replicated field trials. Moreover, the effect can be evaluated under a variety of environmental conditions (e.g. optimal or stress induced environments). Evaluation of transgene effects can be accomplished on a large scale—thousands to tens of thousands of genes per year, at a dramatically lower cost (because of reduced manpower and field resources), and far more quickly than traditional transgene function testing methods (such as, e.g. in yield trials).

A "yield related trait" may include but is not limited to any of the following traits: leaf angle, anthesis-silking interval (ASI), staygreen ability, early growth rate, overall growth rate, maximum biomass, total biomass, nitrogen stress tolerance, and drought tolerance. Preferably, the yield related trait is biomass, nitrogen stress tolerance, or drought tolerance.

The maize plants may contain a transgene of interest and are otherwise referred to herein as "transgenic plants". The term "transgenic plant" refers to a plant which comprises within its genome one or more heterologous polynucleotides. For example, the heterologous polynucleotide is stably integrated within the genome such that the polynucleotide is passed on to successive generations. The heterologous polynucleotide may be integrated into the genome alone or as part of a recombinant DNA construct. Each heterologous polynucleotide may confer a different trait to the transgenic plant.

Plants may be grown using any of a number of experimental designs that will reduce or eliminate sources of experimental error. Some examples of designs include but are not limited to: one-factor designs, nested designs, factorial designs, randomized block designs, split plot designs, repeated measure designs, and unreplicated designs. One of ordinary skill in the art would be familiar with these and other experimental designs.

Plants may be grown under water limiting conditions. "Water limiting conditions" refers to a plant growth environment where the amount of water is not sufficient to sustain optimal plant growth and development. One skilled in the art would recognize conditions where water is sufficient to sustain optimal plant growth and development. The terms "drought" and "water limiting conditions" are used interchangeably herein.

When a genotype yields better than another under water-limiting conditions, the plant is generally referred to as being "drought tolerant." "Drought tolerance" is a trait of a plant to survive under drought conditions over prolonged periods of time without exhibiting substantial physiological or physical deterioration. "Drought" refers to a decrease in water availability to a plant that, especially when prolonged, may cause damage to the plant or prevent its successful growth (e.g., limiting plant growth or seed yield).

A "drought tolerant plant" is a plant that exhibits drought tolerance. A drought tolerant plant may be a plant that exhibits an increase in at least one physical property of an immature ear of the plant, relative to an immature ear from a control plant under water limiting conditions.

One of ordinary skill in the art is familiar with protocols for simulating drought conditions and for evaluating drought tolerance of plants that have been subjected to simulated or naturally-occurring drought conditions. For example, one may simulate drought conditions by giving plants less water than normally required or no water over a period of time. A drought stress experiment may involve a chronic stress (i.e., slow dry down) and/or may involve two acute stresses (i.e., abrupt removal of water) separated by a day or two of recovery. Chronic stress may last 8-10 days. Acute stress may last 3-5 days.

Plants may be grown under nitrogen limiting conditions. "Nitrogen limiting conditions" refers to a plant growth environment where the amount of total available nitrogen (e.g., from nitrates, ammonia, or other known sources of nitrogen) is not sufficient to sustain optimal plant growth and development. One skilled in the art would recognize conditions where total available nitrogen is sufficient to sustain optimal plant growth and development. One skilled in the art would recognize what constitutes sufficient amounts of total available nitrogen, and what constitutes soils, media and fertilizer inputs for providing nitrogen to plants. Nitrogen limiting conditions will vary depending upon a number of factors, including but not limited to, the particular plant and environmental conditions.

When a genotype yields better than another under nitrogen limiting conditions, the plant is generally referred to as being "nitrogen stress tolerant." "Nitrogen stress tolerance" is a trait of a plant and refers to the ability of the plant to survive under nitrogen limiting conditions.

A "nitrogen stress tolerant plant" is a plant that exhibits nitrogen stress tolerance. A nitrogen stress tolerant plant may be a plant that exhibits an increase in at least one physical property of an immature ear of the plant, relative to an immature ear from a control plant under nitrogen limiting conditions.

One of ordinary skill in the art is familiar with protocols for simulating nitrogen stress conditions and for evaluating nitrogen stress tolerance of plants that have been subjected to simulated or naturally-occurring nitrogen limiting conditions.

Some methods of the disclosure involve a destructive assay. Thus, plants that are genetically similar to plants evaluated using the methods of the disclosure such as for instance, plants containing the same construct or inbreds or hybrids with the same genetic composition, can be selected and then subjected to further testing for breeding purposes. However, immature ear traits may be assessed in a nondestructive manner. For example, an X-ray scanner/sensor can be used to collect the digital image(s). X-rays can penetrate plant tissues and allow visualization of concealed and/or internal plant parts. Thus, intact immature ears still on the plant and/or inside husk leaves may be assayed for physical properties of the ear that may otherwise require destructive sampling of the ear.

Methods of evaluating an immature reproductive part of a crop plant to assess the effect of a transgene or a recombinant nucleic acid construct on seed yield in the crop plant are also presented. In these methods, digital images of the immature reproductive part of the crop plant are obtained without physically removing the part from the crop plant, and the digital images are analyzed to assess the effect of the transgene or the recombinant nucleic acid construct on seed yield.

The crop plant may be maize, soybean, sorghum, canola, wheat, rice, or barley. The reproductive part may be an ear, a pod, a seed head, a spikelet or spike, or any seed bearing structure known to one of ordinary skill in the art.

The transgene may be overexpressed.

The recombinant nucleic acid construct may be an RNAi construct.

EXAMPLES

The following examples are offered to illustrate, but not to limit, the claimed disclosure. It is understood that the examples and embodiments described herein are for illustrative purposes only, and persons skilled in the art will recognize various reagents or parameters that can be altered without departing from the spirit of the disclosure or the scope of the appended claims.

Example 1

Image Analysis Data Evaluation Method as Applied to Transgenic Plants

Plant Material

T0 plants are grown from maize callus that has been transformed with a construct containing a gene of interest. T0 sister plants are obtained from the same callus, and one or more plants are grown in a an environmentally-controlled greenhouse for evaluation of one or more traits, including length, width, area, kernel number per ear, biomass, and specific growth rate. T0 plants are selected based on trait performance, and the sister plants of the selected T0 plants are then crossed with GASPE Flint, a fast growing, short stature inbred to obtain T1 seeds.

Growing Conditions and Transgene Testing

T1 seeds are sown in a 50% Turface and 50% SB300 soil mixture at a uniform depth of 2" from the surface and a planting density of 8.5" between plants (~72K plants/acre). Each T1 plant is grown in a classic 200 size pot (volume equivalent to 1.7 L) and tagged with a bar code label that contains information about the plant's genetic identity, planting date and greenhouse location. Transgenic plants and their non-transgenic segregants are distinguished using DsRED fluorescence screening or ELISA strip tests that detect the presence of a marker gene linked with a gene of interest.

Experimental Design

A split block design with stationary blocks is used to minimize spatial variation. Multiple events are evaluated for each construct, and for each event, 15 transgene positive and 15 transgene negative plants are used. Positives and negatives are completely randomized within each event block. The transgene negative plants from events of the same construct are pooled together and used as the construct null, which represents the control.

Immature Ear Harvesting

Ear shoots are covered with a shoot bag to prevent pollination and are monitored for $1^{st}$ day of silk-exertion. Immature (un-pollinated) ears are then harvested at 8 days after initial silking and placed in a shoot-bag or other suitable container, labeled with a bar-code tag containing the sample-identification-number and any other info needed for sampled recognition.

Image Acquisition

Immature ears are either hand or machine harvested at maturity and a digital image may be taken under controlled lighting conditions. The image may be taken of one or more immature ears of maize. The use of controlled lighting is not required, but provides standardized conditions, thereby simplifying the image analysis process. Without controlled lighting conditions, algorithmic or manual determinations of lighting conditions may be made and additional calibrations may be performed to assist in providing proper image processing conditions. The quality of the image (lighting, contrast, color balance, color fidelity etc.) can also be manipulated to improve the image for analysis purposes.

To acquire images, various types of image sensors may be used. The image sensors used may include a charge coupled device (CCD) image sensor, a camera, video camera, color sensor, laser/light beam sensor, ultrasonic sensor, an X-ray scanner/sensor, or other type of image sensor. The current imaging sensor uses a commercially available digital camera with detection of the visible light spectrum. However, the image sensor may provide for imaging across a spectrum wider than or different from the visible spectrum. The image sensor may be configured to image an entire single ear, multiple ears, or smaller subsections of one or more immature ears. If analog images are directly acquired instead of digital images, then the analog images may be converted to digital images through scanning or other means. Alternatively, the amount of light intercepted as the ear moves through a light field could provide an alternate means of either two or three dimensional data collection.

Image Analysis

Digital image analysis of immature ear photographs is conducted using image processing software to extract data. One example of image processing software that may be used to extract data is Image Pro Plus (Media Cybernetics, Silver Spring, Md.). Various image processing operations may be performed, e.g. techniques or algorithms to delineate image pixels associated with the immature ear object of interest from the general image background and\or extraneous debris. Data information can be recorded for each whole or subsection of immature ear objects including, without limitation, object area, minor axis length, major axis length, width, perimeter, ear color (such as red, blue, green density), silk count, and/or other information regarding ear size, shape, morphology, location, or color (e.g. spikelet number, size distribution, and tapering of ear).

The image analysis process is performed in a fully automated fashion using an algorithm that executes the following steps to achieve binary segmentation of the ear object from background or foreign material and produce useable measurement data output.

1. The subject image is compared to a previously characterized reference image to ensure the image capture process was conducted according to a set protocol and that expected spectral characteristics of the subject ear objects are within tolerance of the image analysis procedures to achieve acceptable results.
2. Deviations from expected image quality are addressed either by triggering an automatic spectral correction process or by triggering an error handler process that returns information to the process manager that the image is unsuitable for automated analysis. A commercially available standardized color chart such as that shown in FIG. 1 can be used to correct image spectra to desired levels and provides a spatial calibration reference.
3. Once image quality parameters are satisfied, then one or more ear objects are uniquely identified and isolated from the general image background using predefined color and sizing configuration information that isolates the ear object from foreign material and the general background spectrum resulting from the sample holder (tray, table, stage). Alternatively, a digital filtering process can be used to isolate and identify the ear object for data extraction. See FIGS. 1 and 2.
4. Following ear object identification and isolation, a spatial calibration process is applied to convert pixel unit measurements to metric units of measure (e.g cm). The calibrated results are generated automatically and exported to data files for summarization and interpretation into descriptive traits.

FIGS. 1A and 1B are digital images of single and multiple immature ear samples of maize, respectively. These digital images are representative of the input image samples to process. FIGS. 2A and 2B illustrate the results of the segmentation processing to isolate the immature ear object pixels from the background pixels. Once the ear object pixels have been identified on the image, measurements are collected and data output is created. Example data output for a single ear are shown in Table 1.

TABLE 1

Example single ear data output

| Image Name | Major axis length (cm) | Minor axis length (cm) | Area (cm$^2$) | Perimeter (cm) |
|---|---|---|---|---|
| AB123.JPG | 6.9 | 2.4 | 11.7 | 16.7 |

Example 2

Reproducibility of Immature Ear Photometry Data

To evaluate the reproducibility of immature ear photometry, ten immature ears with lengths ranging from 4 to 24 cm were imaged ten times each, removing the ear and replacing it between each photo. The coefficient of variation (CV) for ear length ranged from 0.3-2.2%, with an average value of 0.9%. The coefficient of variation for ear area ranged from 0.6-6.8% and averaged 2.1%. Factors noted to increase variability included asymmetry of the ear and shading from the camera flash used to illuminate the sample chamber. Radial asymmetry of the ear can slightly affect width and area. Shading from the flash is usually noted on very long ears and can increase variability on ear length and area. In the limited set under analysis, asymmetry led to a nearly three-fold greater increase in variability of ear area than shading, thereby demonstrating that "natural" variability of material under study is a larger contribution to variability of measured parameters than variability introduced by camera system parameters.

Example 3

Immature Ear Photometry Data Analysis Under Low Nitrogen Conditions

To explore the feasibility of using immature ear photometry data to assess T1 plants in a low nitrogen (LN) assay, wild type (non-transgenic) plants were grown in Classic 200 size pots (volume equivalent to 1.7 L) and labeled with a barcode with information about the plant's genetic identity, planting date and greenhouse location. Seeds were sown in 100% Turface MVP soil-less medium at a uniform depth of 2" from the surface and a planting density of 8.5" between plants (~72K plants/acre). Fourteen days after planting, automated watering with low or high nitrogen liquid fertilizer was initiated and continued until harvest. At time of silk emergence, ears were bagged to prevent pollination. Ears were harvested 8 days after silk emergence and analyzed with ear photometry. Several photometric parameters (e.g. immature ear area and immature ear length; Table 2) showed more than 40% reduction under low nitrogen yet maintained relatively low coefficients of variation (CV).

TABLE 2

Ear photometry variables and CVs under low and normal nitrogen conditions

| Variable | CV under low N | CV under normal N | % reduction from normal N |
|---|---|---|---|
| Immature Ear Area | 17.0% | 20.0% | 49.9% |
| Immature Ear Length | 13.8% | 14.2% | 42.3% |

Example 4

Performance Analysis of T0 Leads in T1 Low Nitrogen Assay

A low nitrogen assay was applied to transgenic plants and their non-transgenic segregants. A split block design with stationary blocks was used to minimize spatial variation. Four events for each construct (with each construct containing a lead gene for evaluation) were chosen for the T1 assay. For each event 15 transgene positive and 15 transgene negative plants were used. Positives and negatives were randomly paired within each event block. All constructs (PHPs) used in the T1 assay were constructs that performed positively or negatively at the T0 stage (i.e. significantly positive or negative at P<0.1 for two or more ear photometry traits at T0 phenotypic assay).

The T1 low nitrogen results are shown in Table 3. A significant call at T1 was made when two or more out of four events tested were significantly positive or negative for at least one ear photometry trait. Among the four significantly positive constructs selected based on T0 ear photometry data, one (PHPXX708) was also significantly positive in the T1 low nitrogen assay. In addition, one (PHPXX560) of the four significantly negative leads was confirmed in the T1 low nitrogen assay.

TABLE 3

Construct performance in T0 and T1 low nitrogen assays

| PHP | T0 LN assay | T1 LN assay |
|---|---|---|
| PHPXX712 | Significantly positive | Neutral |
| PHPXX563 | Significantly positive | Neutral |
| PHPXX708 | Significantly positive | Significantly positive |
| PHPXX626 | Significantly positive | Neutral |
| PHPXX560 | Significantly negative | Significantly negative |
| PHPXX570 | Significantly negative | Neutral |
| PHPXX569 | Significantly negative | Neutral |
| PHPXX701 | Significantly negative | Neutral |

Example 5

Immature Ear Photometry Data Analysis Under Drought Conditions

To explore the feasibility of using immature ear photometry data to assess T1 plants in a drought assay, wild type (non-transgenic) plants were grown in Classic 200 size pots (volume equivalent to 1.7 L) labeled with a bar coded label containing information about the plant's genetic identity, planting date and greenhouse location. Seeds were sown in 50% Turface and 50% SB300 soil mixture at a uniform depth of 2" from the surface and a planting density of 8.5" between plants (~72K plants/acre). At 10% tassel emergence automated watering was discontinued for approximately 10 days. After 10 days regular watering resumed. At time of silk emergence, ears were bagged to prevent pollination. Ears were harvested 8 days after silk emergence and analyzed with ear photometry (data shown in Table 4).

TABLE 4

Ear photometry variables and CVs under drought and well-watered conditions

| Parameter | CV under drought | CV under WW | % Reduction from WW |
|---|---|---|---|
| Immature Ear Area | 28.30% | 26.00% | 44.10% |
| Immature Ear Length | 19.50% | 19.90% | 31.90% |

Example 6

Performance Analysis of T0 Leads in T1 Drought Assay

Drought stress was applied by delivering a minimal amount of liquid fertilizer daily for an extended period of time. Transgenic plants and their non-transgenic segregants were identified through strip tests used to assay the presence of a marker gene linked with the gene of interest. A split block design with stationary blocks was used to minimize spatial variation. Six events from each constructs were chosen for the T1 assay. For each event 15 transgene positive and 15 transgene negative plants were used. Positives and negatives were randomly paired within each event block. All constructs (PHPs) used in the T1 assay were constructs that performed positively or negatively in the T0 generation (significantly positive or negative at P<0.1 for two or more ear photometry traits at T0 phenotypic assay). The T1 drought assay results are shown in Table 5. A significant call at T1 was made when two or more out of the six events tested significantly positive or negative for at least one ear photometry trait. Among the 10 significantly positive constructs selected based on T0 ear photometry data; seven were significantly positive in the T1 drought assay. Three of the six significantly negative constructs from the T0 drought assay also were significantly negative in the T1 drought assay.

TABLE 5

Construct performance in T0 and T1 drought assays

| PHP Name | T0 Drought Assay | T1 Drought Assay |
|---|---|---|
| PHPXX316 | Significantly positive | Neutral |
| PHPXX351 | Significantly positive | Significantly positive |
| PHPXX354 | Significantly positive | Neutral |
| PHPXX355 | Significantly positive | Significantly positive |
| PHPXX356 | Significantly positive | Significantly positive |
| PHPXX357 | Significantly positive | Significantly positive |
| PHPXX359 | Significantly positive | Significantly positive |
| PHPXX562 | Significantly positive | Significantly positive |
| PHPXX572 | Significantly positive | Neutral |
| PHPXX595 | Significantly positive | Significantly positive |
| PHPXX558 | Significantly negative | Significantly positive |
| PHPXX565 | Significantly negative | Significantly negative |
| PHPXX580 | Significantly negative | Significantly positive |
| PHPXX582 | Significantly negative | Neutral |
| PHPXX601 | Significantly negative | Significantly negative |
| PHPXX627 | Significantly negative | Significantly negative |

Example 7

Correlation of Immature Ear Parameters and Yield in the Field

Two experiments were performed to assess the correlation between yield and ear parameters at two stages of development, the R1 (silk emergence; equivalent to the immature ear stage) and physiological maturity. One experiment was conducted in soil that had been depleted for nitrogen ("depleted") and another was done in soil with a historically normal nitrogen management ("non depleted"). In both experiments, nitrogen fertilizer was applied at the V3 stage of development. The experiment conducted under depleted conditions consisted of a single commercial hybrid 33W84 and four fertilization treatments at rates of 0, 20, 40 and 60 lbs of N per acre. There were 4 replicates of all treatment combinations. The second experiment conducted under non depleted conditions consisted of three hybrids (subplot), 33W84, 33T56 and 33K42, confounded within the main plots and five fertilization treatments (Main Plot) at rates of 0, 30, 60, 90, 120 and 150 lb N per acre. There were five replicates of each treatment combination.

Ten plants of each plot were sampled at R1 and at physiological maturity. At R1 the parameters measured were SPAD, immature ear weight, immature ear length, immature ear width and total plant biomass. At physiological maturity the parameters measured were ear weight, 100 kernel weight, kernel number, grain weight and total biomass. All measurements were expressed on a per plant basis. Analysis of variance was conducted for each experiment to determine significance of main plots, subplots and mainplot×subplot interactions, where appropriate.

In both depleted and in non-depleted plots across varying nitrogen fertility levels, grain yield per plant was significantly related to the ear length and/or ear weight at R1 (silking) (FIGS. 3-6).

Example 8

Use of Immature Ear Photometry to Select Maize Plants with Desirable Agronomic Characteristics Maize plants, e.g. inbred or hybrid maize plants, can be planted in the greenhouse or in the field, and immature ears can be obtained for image acquisition and analysis (described in EXAMPLE 1), e.g. when the first silks are visible (i.e. when the range of silks is 1 to 50). Maize plants can then be compared to one another as well as to controls for a number of immature ear characteristics including but not limited to object area, minor axis length, major axis length, width, perimeter, ear color (such as red, blue, green density), silk count, and/or other information regarding ear size, shape, morphology, location, or color (e.g. spikelet number, size distribution, and tapering of ear). In this way, maize plants can be sorted for a desired agronomic characteristic and then selected for breeding purposes.

Example 9

Figure 7:
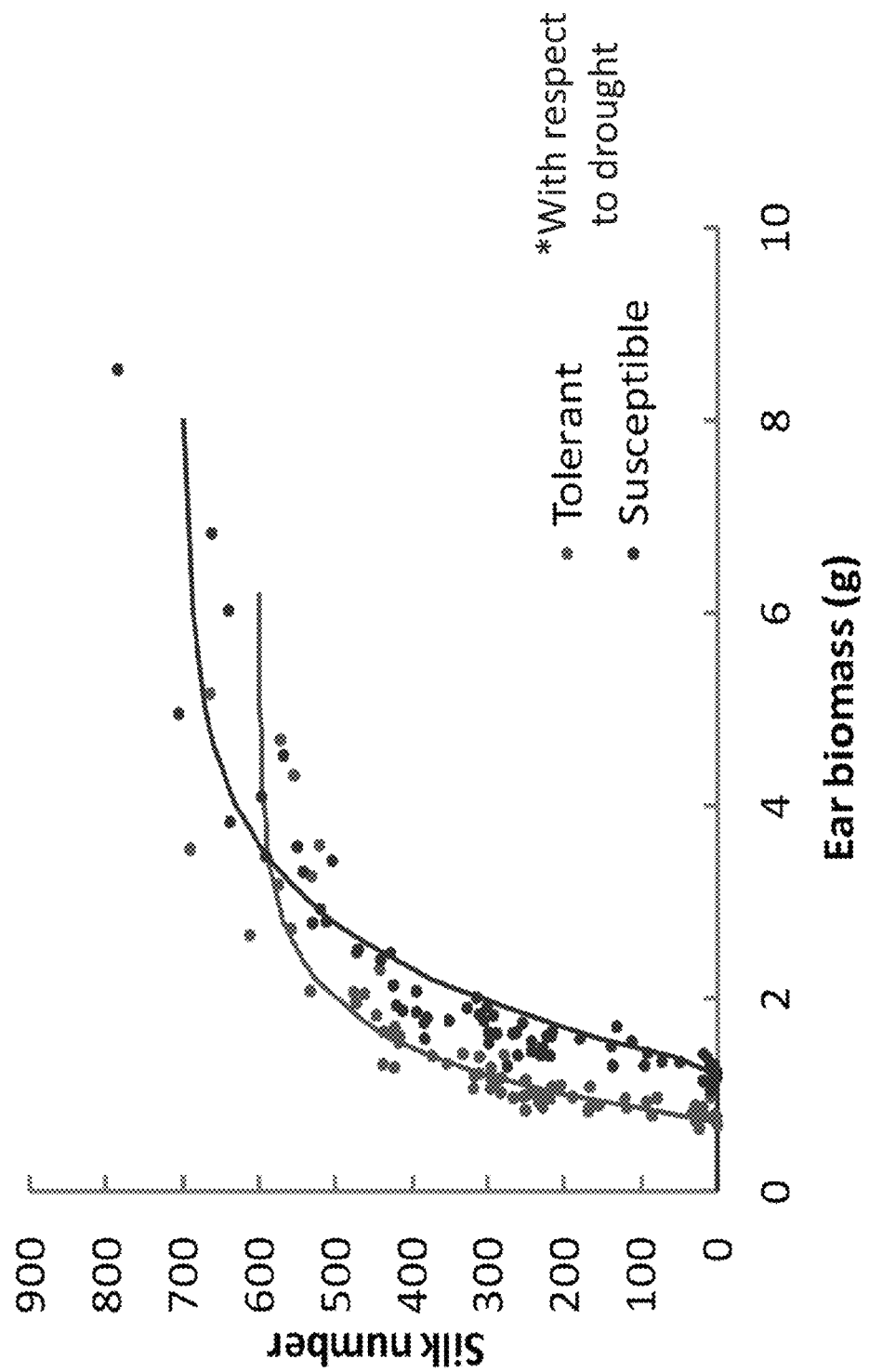
FIG. 7 shows the relationship between silk number and ear biomass for two hybrids with contrasting performance under drought stress conditions.

Use of Immature Ear Photometry to Select Maize Plants with Increased Yield Under Drought Stress During approximately the first ten days after the first pistillate flower becomes visible, as it emerges out of the husks, there is a strong relationship between the number of emerged flowers (i.e. silk number) and ear biomass. This relationship is useful to separate drought tolerant from drought susceptible maize hybrids (FIG. 7) since drought tolerant hybrids tend to have smaller ears at this stage of development as compared to drought susceptible hybrids.

Figure 8:
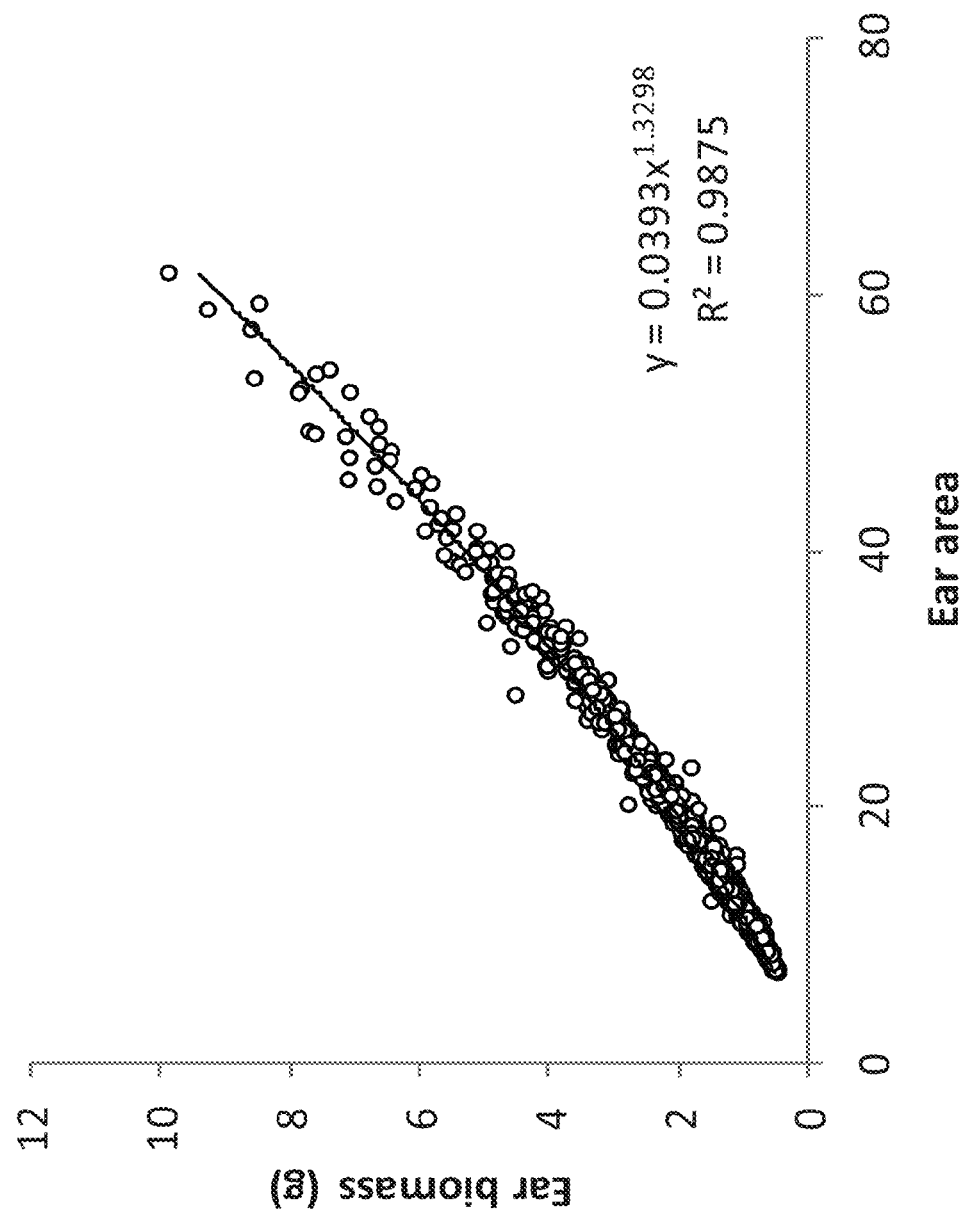
FIG. 8 shows the relationship between ear biomass and ear area measured in field experiments conducted at Viluco research station in 2010-2011 growing season.
Figure 9:
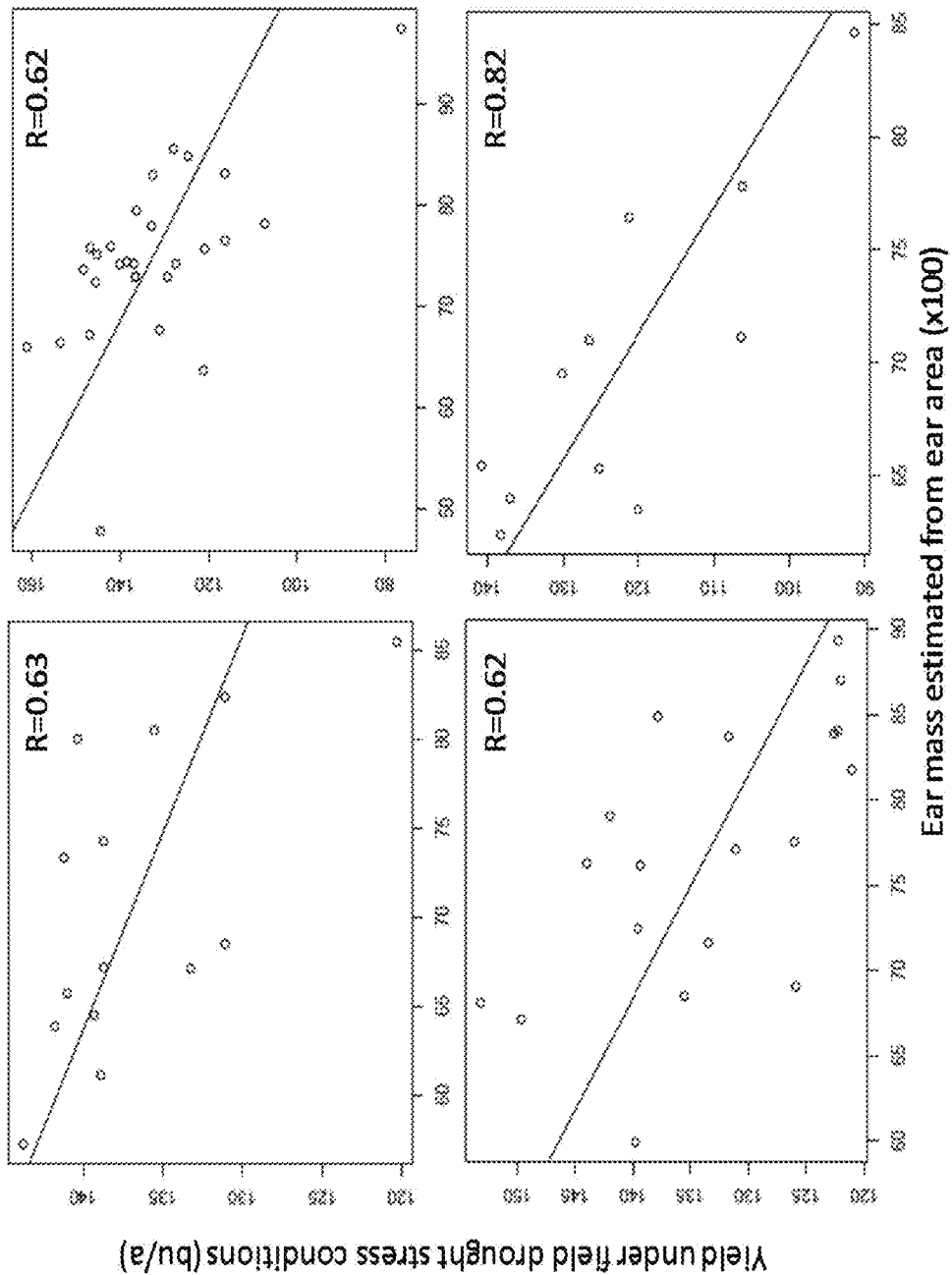
FIG. 9 shows the relationship between ear biomass, estimated from ear area (×100 g) at the immature ear stage, and yield under field drought stress conditions (bu/a) for three breeding populations.

Because of the relationship between ear biomass and drought tolerance at the immature ear stage and the fact that there is a close association between ear area and ear biomass (FIG. 8), immature ear area can be used to characterize breeding populations for drought tolerance. Thus, biomass can be estimated from ear area at the immature ear stage and then maize inbreds and/or hybrids with smaller ear area can be selected as having increased drought tolerance. FIG. 9 shows the relationship between immature ear biomass, which was estimated from immature ear area, and yield under drought stress conditions for three breeding populations.

Example 10

Leads Selected Using Immature Ear Photometry Show Enhanced Yield in the Field as Compared to Controls PHPXX708 was significantly positive in the T1 low nitrogen assay (Table 3). Among the four events evaluated (Table 6), at least two events showed significantly positive effects for immature ear area; at least two events showed significantly positive effects for immature ear length; and at least two events showed significantly positive effects for immature ear width. Moreover, one of the events showed a significant increase in silk count as compared to the null.

TABLE 6

PHPXX708 Performance in T1 NUE Assay

| | | Percent increase vs. null | | | |
| --- | --- | --- | --- | --- | --- |
| PHP Name | Event Name | ear area 8DAS (sq cm) | ear length 8DAS (cm) | ear width 8DAS (cm) | silk count |
| PHPXX708 | XXXXXX.256.1.2 | 11.80%* | 8.80%* | 5.10%* | 4.90% |
| PHPXX708 | XXXXXX.256.1.3 | 5.30% | 2.60% | 4.10%* | 8.60% |
| PHPXX708 | XXXXXX.256.1.5 | −1.10% | 2.90% | 2.70% | −5.00% |
| PHPXX708 | XXXXXX.256.1.7 | 17.10%* | 16.60%* | −3.70% | 16.80%* |

*indicates significant increase (p < 0.1)

Moreover, PHMXX558 was significantly positive in the T1 drought assay. At least two of five events containing PHPXX558 had significantly positive effects for immature ear area; at least two of the events had significantly positive effects for immature ear width; at least one had a significantly longer ear; and at least one had a significantly higher silk count (Table 7).

TABLE 7

PHPXX558 Performance in T1 Drought Assay

| | | Percent increase vs null | | | |
| --- | --- | --- | --- | --- | --- |
| PHP Name | Event Name | ear area 8DAS (sq cm) | ear length 8DAS (cm) | ear width 8DAS (cm) | silk count |
| PHPXX558 | XXXXXX.242.2.1 | 14.30% | 6.50% | 9.20%* | −1.70% |
| PHPXX558 | XXXXXX.242.2.3 | 25.50%* | 18.70%* | −1.40% | 29.10%* |
| PHPXX558 | XXXXXX.242.2.5 | 5.10% | 0.30% | 4.80% | 13.40% |
| PHPXX558 | XXXXXX.242.2.6 | 21.30%* | 8.00% | 8.90%* | 10.90% |
| PHPXX558 | XXXXXX.242.2.7 | 15.50% | −3.10% | 10.30%* | 10.40% |
| PHPXX558 | XXXXXX.242.2.9 | 3.00% | −0.70% | 2.50% | 3.60% |

*indicates significant increase (p < 0.1)

The same lead gene is present in constructs PHPXX708 and PHPXX558. Constructs containing that specific lead gene were generated and then introduced into elite maize. Single copy homozygous transgenic inbred corn plants containing the transgene were crossed with a tester line to produce hybrid seed. The resulting seed was advanced to yield trials in multiple locations under drought or low N environments. Transgenic events and wild-type plants were planted at the same plant density. Hybrids overexpressing the transgene yielded more than the controls (wild-type) when averaged across all events in locations under drought and low N conditions as well as in well watered environments. In addition, several events yielded significantly better than controls in many yield trial locations (data not shown).

Example 11

Immature Ear Photometry to Obtain Spikelet Counts

Spikelet counts may be obtained manually, and corrections to the counts may be performed using an image processing algorithm. Spikelet number is related to yield, so spikelet counts obtained through immature ear photometric analysis can aid in selecting plants with improved yield potential as part of a plant breeding program.

Example 12

Non-Destructive Collection of Immature Ear Parameters Using X-Ray Imaging

The collection of immature ear parameters, as detailed in the methods and examples herein, may also be obtained in a nondestructive manner using an X-ray scanner/sensor to collect the digital image(s).

For example scans of immature ears can be obtained using axial three dimensional computed tomography. Several ears can be placed inside a CFRP (carbon fiber reinforced polymer) tube. Two dimensional images can then be obtained, and the images can be subject to binary segmentation. An average of the 2-D binarized slices can be obtained to get the maximum outline of an ear. Traits such as but not including immature ear length and diameter can be evaluated using the averaged projection. FIG. 10 shows raw images of immature ears obtained from X-ray imaging.

What is claimed is:

1. A method of evaluating a maize plant comprising:
   a. acquiring a digital image of an immature ear of said maize plant;
   b. processing the digital image;
   c. determining at least one physical property of the immature ear from the processed digital image; and
   d. evaluating the maize plant based on the at least one physical property of the immature ear.

2. The method of claim 1, wherein the at least one physical property of the immature ear is area, length, width, perimeter, ear color, silk count, spikelet number, size distribution, or tapering of the ear.

3. The method of claim 1, wherein the image is processed using binary segmentation.

4. The method of claim 1, wherein the digital image is acquired using an image sensor.

5. The method of claim 4, wherein the image sensor is selected from the group consisting of: a charge coupled device (CCD) image sensor, a digital camera, a video camera, a color sensor, a laser/light beam sensor, an X-ray scanner/sensor, and an ultrasonic sensor.

6. The method of claim 4, wherein the digital image acquired using an image sensor is acquired under controlled lighting conditions.

7. The method of claim 4, wherein the digital image acquired using an image sensor is acquired using algorithmically or manually determined lighting conditions.

8. The method of claim 4, wherein the image sensor is configured to image one or more immature ears in their entirety or smaller subsections of one or more immature ears.

9. The method of claim 1, wherein the digital image is acquired by scanning an analog image.

10. The method of claim 1, wherein said digital image is acquired non-destructively.

11. The method of claim 1, further comprising predicting mature ear yield for the maize plant based on the at least one physical property of the immature ear.

12. The method of claim 1, wherein the maize plant is evaluated for yield and/or a yield related trait.

13. The method of claim 12, wherein the maize plant comprises a transgene of interest or a recombinant nucleic acid construct.

14. The method of claim 13, wherein the maize plant comprising a transgene of interest or a recombinant nucleic acid construct is evaluated as compared to other maize plants in a population of transgenic maize plants to assess the effect of the transgene or the recombinant nucleic acid construct on yield or a yield-related trait.

15. The method of claim 14, wherein the population of transgenic plants has been generated using a fast cycling uniform maize line.

16. The method of claim 13, wherein the transgene is overexpressed.

17. The method of claim 13, wherein the recombinant nucleic acid construct is an RNAi construct.

18. The method of claim 12, wherein the yield related trait is selected from the group consisting of biomass, nitrogen stress tolerance, and drought tolerance.

19. The method of claim 12, wherein the maize plant is grown under nitrogen and/or water limiting conditions.

* * * * *